(12) United States Patent
Petrenko et al.

(10) Patent No.: US 9,068,952 B2
(45) Date of Patent: Jun. 30, 2015

(54) METHOD AND APPARATUS FOR PRODUCING AND MEASURING DYNAMICALLY FOCUSSED, STEERED, AND SHAPED OBLIQUE LASER ILLUMINATION FOR SPINNING WAFER INSPECTION SYSTEM

(75) Inventors: Aleksey Petrenko, Milpitas, CA (US); Christian Wolters, Campbell, CA (US); Zhongping Cai, Fremont, CA (US); Anatoly Romanovsky, Palo Alto, CA (US); Bret Whiteside, Gilroy, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 821 days.

(21) Appl. No.: 12/584,294

(22) Filed: Sep. 2, 2009

(65) Prior Publication Data

US 2011/0051132 A1 Mar. 3, 2011

(51) Int. Cl.
*G01N 21/88* (2006.01)
*G01N 21/95* (2006.01)
*G02B 27/09* (2006.01)

(52) U.S. Cl.
CPC ........ *G01N 21/9501* (2013.01); *G01N 21/8806* (2013.01); *G02B 27/0972* (2013.01)

(58) Field of Classification Search
USPC .......................................... 356/237.2–237.6
See application file for complete search history.

(56) References Cited

U.S. PATENT DOCUMENTS

| | | | |
|---|---|---|---|
| 4,987,303 A * | 1/1991 | Takase et al. ...................... 850/5 |
| 5,672,885 A * | 9/1997 | Allen et al. ................. 250/559.3 |
| 6,201,601 B1 * | 3/2001 | Vaez-Iravani et al. ...... 356/237.4 |
| 6,426,502 B1 | 7/2002 | Finarov |
| 6,734,967 B1 | 5/2004 | Piwonka-Corle |
| 6,853,446 B1 * | 2/2005 | Almogy et al. ............ 356/237.1 |
| 6,888,638 B1 | 5/2005 | Hill |
| 6,891,611 B1 * | 5/2005 | Vaez-Iravani et al. ...... 356/237.4 |
| 2005/0219518 A1 * | 10/2005 | Korngut et al. ............. 356/237.2 |
| 2007/0182958 A1 | 8/2007 | Manabe |

FOREIGN PATENT DOCUMENTS

| | | |
|---|---|---|
| JP | 09-295178 A | 11/1997 |
| JP | 2007240512 A | 9/2007 |
| KR | 10-2000-0074978 A | 12/2000 |

* cited by examiner

*Primary Examiner* — Rebecca C Bryant
(74) *Attorney, Agent, or Firm* — Deborah Wenocur

(57) ABSTRACT

A method and apparatus for producing high frequency dynamically focused oblique laser illumination for a spinning wafer inspection system. The focus is changed by changing the beam direction incidence angle so as to bring focal spot onto the wafer surface.

Disclosed herein is a system and method for automatic beam shaping (i.e., spot size) and steering (i.e., position) for a spinning wafer inspection system, combined into a single module. Also disclosed is a method and system for measuring the beam position/size/shape and angle with sufficient resolution to make corrections using feedback from the monitor.

9 Claims, 10 Drawing Sheets

US 9,068,952 B2

METHOD AND APPARATUS FOR PRODUCING AND MEASURING DYNAMICALLY FOCUSSED, STEERED, AND SHAPED OBLIQUE LASER ILLUMINATION FOR SPINNING WAFER INSPECTION SYSTEM

FIELD OF THE INVENTION

This invention pertains to wafer inspection systems for semiconductor processing, and in particular to illumination for spinning wafer inspection systems.

BACKGROUND OF THE INVENTION

The development of spinning wafer inspection systems has been an important tool as wafer sizes increase and maintaining throughput becomes increasingly challenging. For most equipment designs, throughput scales roughly linearly with inspected area. The use of the spinning inspection system which employs a spiral scan in place of earlier linear scans permits the most complete scan of the wafer without wasting inspection time. Furthermore, scanning data is output as a single data stream, which simplifies data processing.

As the technology of spinning wafer inspection systems evolves, higher sensitivity defect detection is desired. Higher sensitivity is achieved with shorter wavelength illuminating light and using smaller spot size. This results in a smaller depth of focus, i.e., the sample goes out of focus more easily. FIG. 1 shows a graph of DOF vs. spot size for three different illumination wavelengths. However, the inherent flatness of the wafer and the chuck may not be within the target depth of focus (the defect detection tool is required to be able to scan wafers with non-flatness of 100 um), therefore the surface of the wafer will not remain in focus and maximum sensitivity cannot be achieved unless a refocusing method is used.

Methods of keeping the laser beam in focus with the spinning wafer include: 1. Moving a beam focusing optical element attached to a servomechanism; and 2. Moving the target surface along the beam to bring it into focus. Both of these aforementioned methods suffer from very slow response time. Typical working frequencies are in the range of 0-100 Hz, which allows correction of disturbances on the order of 10 Hz. The limitation is usually defined by the size of the focusing element. This response time is far below what is needed for state of the art defect detection systems, where wafer spinning is performed at frequencies up to 10000 RPM. A high frequency auto focus system for laser beam scanning devices, to compensate for wafer and chuck motion, would be an important advancement. Correction for slow drift in laser beam position and shape, caused by the laser, the optics, or the mechanics, would also be important.

SUMMARY OF THE INVENTION

Disclosed herein is a method and apparatus for producing high frequency dynamically focused oblique laser illumination for a spinning wafer inspection system. The focus is changed by changing the beam direction incidence angle so as to bring focal spot onto the wafer surface.

In order to accurately focus the beam, as well as to maintain sensitivity, the spot size and position of the illuminating laser beam must be precisely controlled, to compensate for such effects as laser drift or thermal drift. Disclosed herein is a system and method for automatic beam shaping (i.e., spot size) and steering (i.e., position) combined into a single module. Also disclosed is a method a system for measuring the beam position/size/shape and angle with sufficient resolution to make corrections using feedback from the monitor.

BRIEF DESCRIPTION OF THE DRAWINGS

FIG. 4b shows a more detailed illustration of a prism pair of FIG. 4a.

DETAILED DESCRIPTION OF THE INVENTION

Figure 1:
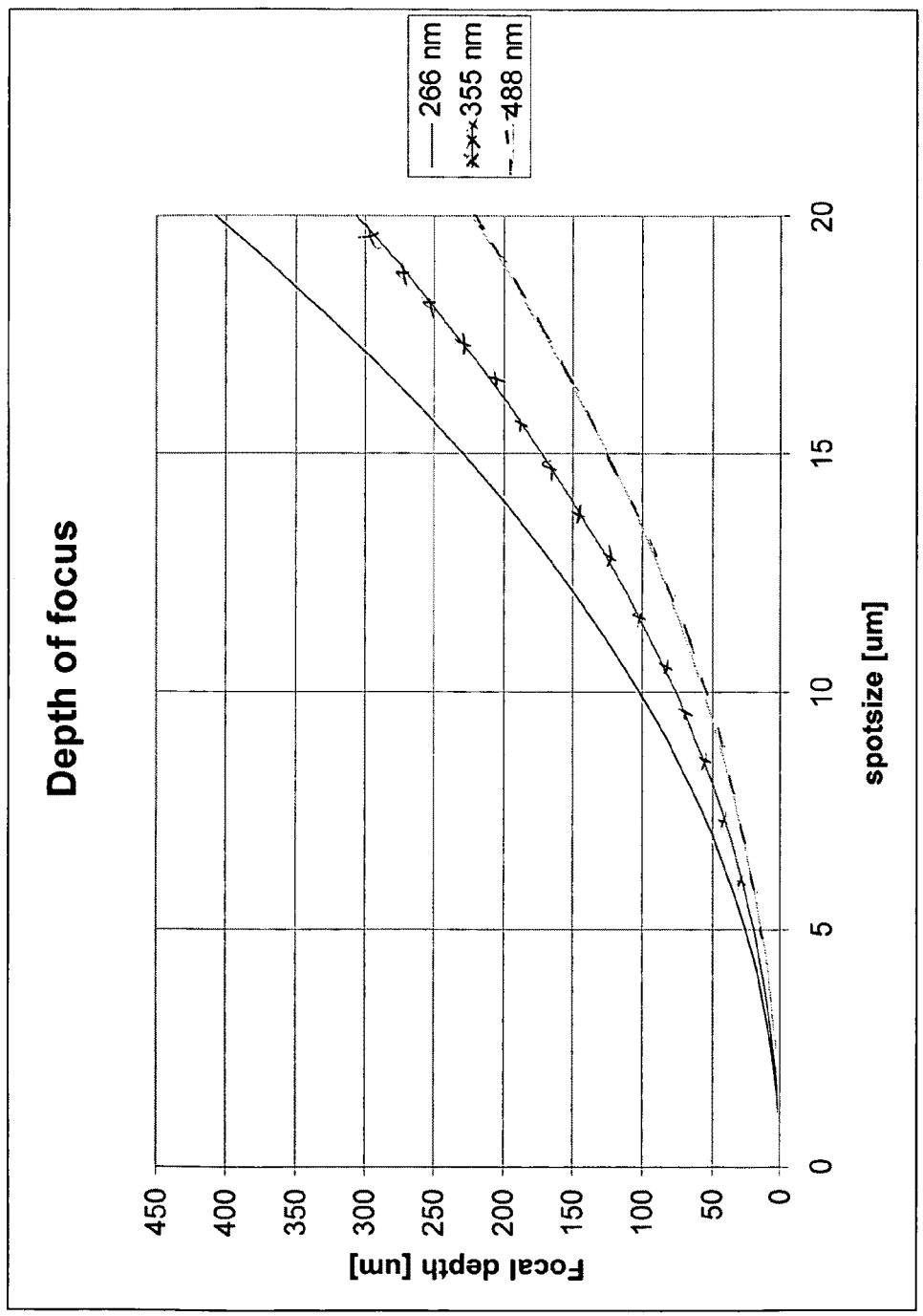
FIG. 1 shows a graph of DOF vs. spot size for three different illumination wavelengths.
Figure 2:
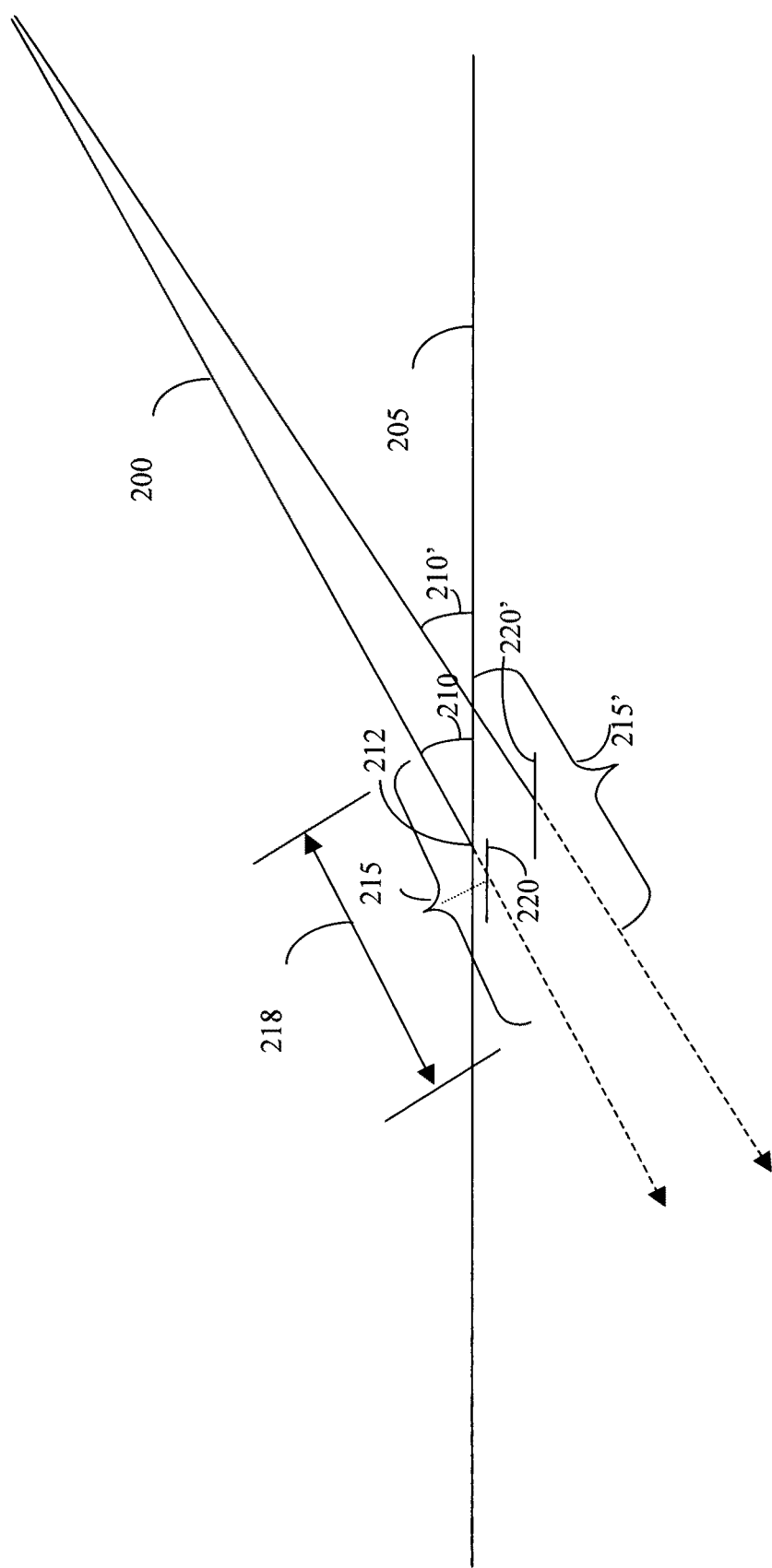
FIG. 2 illustrates the focusing of an oblique incidence illumination beam on an inspection surface.

FIG. 2 illustrates an oblique incidence illumination beam 200, which may be a collimated laser beam, incident on inspection surface 205, which may be the surface of a silicon wafer. Beam 200 impinges on surface 205 at angle 210, and is in focus within region 215, which has depth of focus (DOF) 218. Surface 205 will be in focus if intersection point 212 between surface 205 and beam 200 falls within region 215 (centered at vertical position 220). Note that if the angle of incidence 210 is changed to angle 210', in-focus region 215' has moved, and is centered at a different vertical position 220'. Thus, by dynamically changing the angle 210 of incident beam 200 according to variations in the vertical position of surface 205, focus can be maintained.

Figure 3:
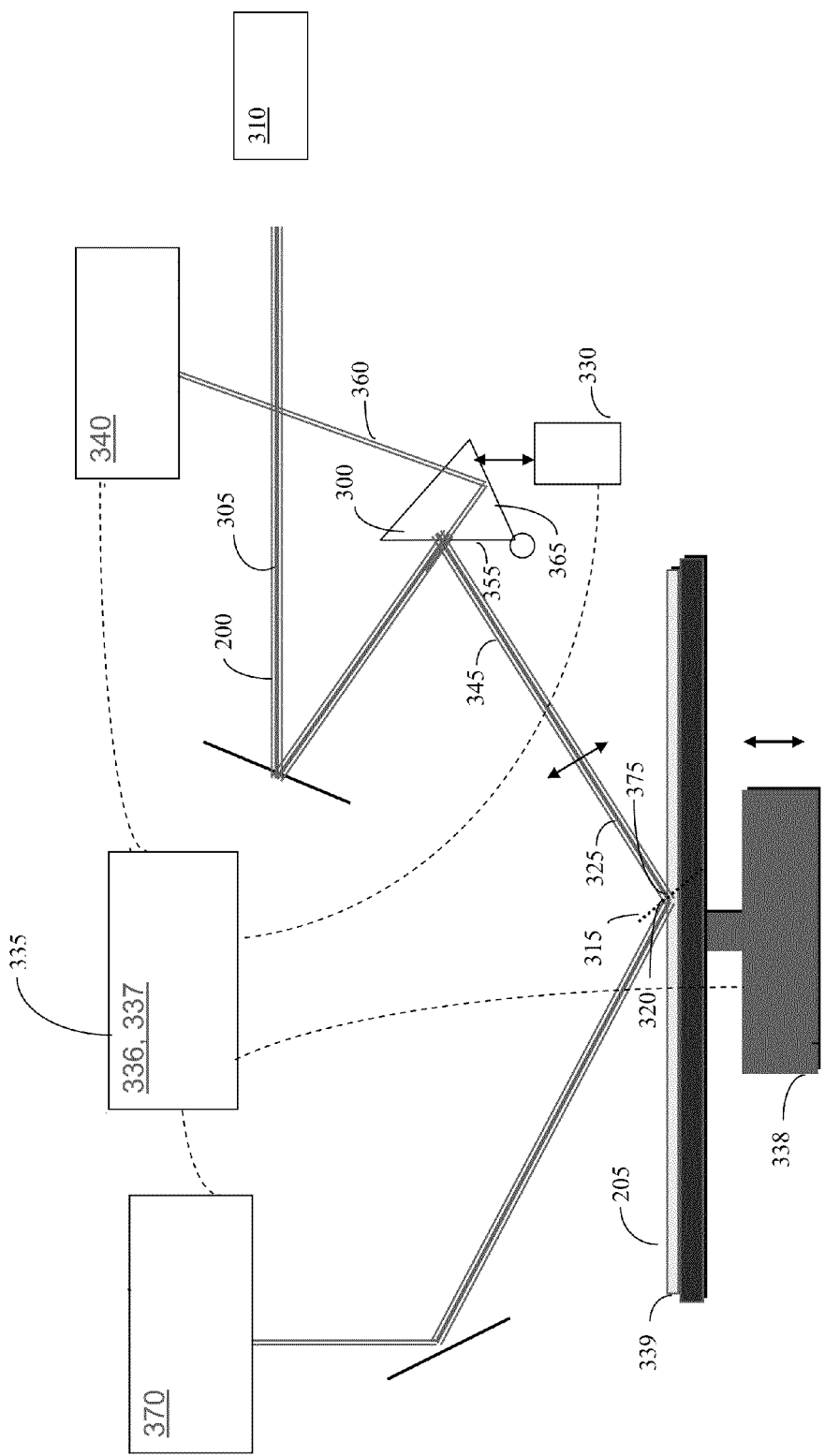
FIG. 3 shows a diagram of an embodiment of the apparatus which controls the inventive autofocus.

FIG. 3 shows a diagram of an embodiment of the apparatus which controls the inventive autofocus. An aspect of the inventive autofocus method is that the collimated laser beam 200 is tilted by a relatively small mirror 300, called the Auto-Focus (AF) mirror, which is off the optical axis 305 of the focusing element 310 but in the path of the incident laser beam. Beam 200 is focused on plane 315 passing the through focal point 320 and perpendicular to optical axis 325. By adjusting the tilt of mirror 300, focal point 320 can be positioned on sample surface 205. The position of the focal point can be calculated as a distance "down the beam" from the AF mirror, assuming that the beam is in the right position relative to the system optics. Then the optimum lateral position for the beam to hit the wafer surface as a function of the surface's instantaneous vertical position can be modeled. Mirror 300 may be mounted on high stiffness piezo actuator 330 with a high voltage amplifier, allowing the autofocus system to achieve working frequencies on the order of thousands of Hz, thereby enabling response times in the order of ms or less. The autofocus system is expected to achieve response times in the range between 0.1-100 ms, corresponding to autofocus frequencies of 10-10,000 Hz. For the purposes of this disclosure, "fast autofocus", which may be alternatley referred to as "high frequency fast autofocus", is defined as operating over the aforementioned frequency range.

A control system 335 generally comprises computing device 336 which may include a high second order PIID (Proportional-Integral-Integral-Derivative) controller, or other types of digital or analog controller including but not limited to: even higher order PID, first order PI, and Fuzzy logic. With the same piezo actuator of limited bandwidth, compared with first order PI, second order PID or even higher order PID helps to shorten the loop response time, and so to achieve smaller following error. Feedforward with notch filter helps to achieve smaller following error further. Control system 335 may interface with the spindle 338 which spins the wafer. In this embodiment, the control system controls and operates the autofocus system, using feedback as follows: The position of the beam on the surface is calculated by two position-sensitive detectors, e.g., cameras. Note that the response time of the detectors must be much smaller than the response time of the tilting mirror. Incident detector 340 detects the position of incident beam 345. This may be accomplished by splitting the incident beam into two beams by prism-shaped mirror 300. In this embodiment, main beam 345 is reflected by front surface 355 of mirror 300 towards sample surface 205. Controlled leakage through front surface 355 forms secondary beam 360. Other possible methods for forming the secondary beam include a pickoff mirror or a beam splitter. Secondary beam 360 is reflected by the inner side of back surface 365 of mirror 300, and is pointed towards incident detector 340. Reflected detector 370 detects the position of main beam 345 reflected by sample surface 205. Options other than a camera for detecting the beam position include but are not limited to: PSD, quad cell, PMT array, diode array, or knife edge with detectors. Readout of (cameras) detectors 340 and 370 is used by computer 336 to calculate (by triangulation) actual beam position, actual position of sample surface 205, and intercept point 375 between the beam and the target surface.

Use of the incident beam position-sensitive detector increases the accuracy of keeping the intercept point at the desired position, and also enables calculation of residual or following error. As described, the camera information may be used to triangulate the intercept point of the beam with the wafer. The ideal intercept point had been determined during system calibration. The difference between ideal and calculated intercept points is used as input parameters for the calculations performed in the autofocus control feedback loop, and in addition, are exported to the data processing unit for further XY correction.

Since the autofocus system causes the incident beam to be deflected according to thickness variations in the sample surface, it is essential that the scan pitch is much smaller than the length scale of the wafer surface variations, so that adjacent scan tracks see almost exactly the same height profile. The autofocus system must also provide a repeatable response, i.e., the same sequence of height errors should result in the same following error. If the ratio of beam size to track pitch is somewhat conservative, in that the track pitch is slightly smaller than needed, it can tolerate small variations of track-track distance. With that, the tracks could be distorted, but adjacent tracks will be distorted in about the same way and the track-track distances will be small.

An additional possible feature of the autofocus system is to combine it with an actuator to cause slower z-motion of the wafer, as is indicated by arrow 378 in FIG. 3. The purpose of this combination is to extend the dynamic range of the fast autofocus, such that on average the fast autofocus operates about its nominal position. This would result in the intercept point where the focus meets the wafer surface, remaining in substantially the same location. It is critical that the slow z-adjustment and the fast AF adjustment work together properly. In an embodiment, the average correction of the AF becomes the control signal for the slow z-motion. If the AF is centered around its nominal value, no z-motion is required. However, if the AF operates for a longer period on one end of the dynamic range, a z-motion command will be issued to bring the AF center back to its nominal value. The response time of the z-motion is typically in the range between 10 ms and 1 s, typically on the order of 100 ms. This range of response time is 1-2 orders of magnitude slower than the range of response times for the AF system, and is therefore defined herein as low frequency.

The autofocus system provides high frequency dynamic adjustment to the beam position and angle of incidence so as to maintain the focus of the incident beam at the wafer surface. Lower frequency adjustments to the beam position, angle, and size are also important, as follows: Optimization of the position and angle of the beam relative to the system optics maximizes intensity and maintains proper collection angles, which becomes important when masks are used that selectively collect angular regions of the scatter. Drift such as laser drift or thermal drift can degrade the signal unless adjustments are made. And if the spot size drifts larger, sensitivity is degraded.

Figure 4A:
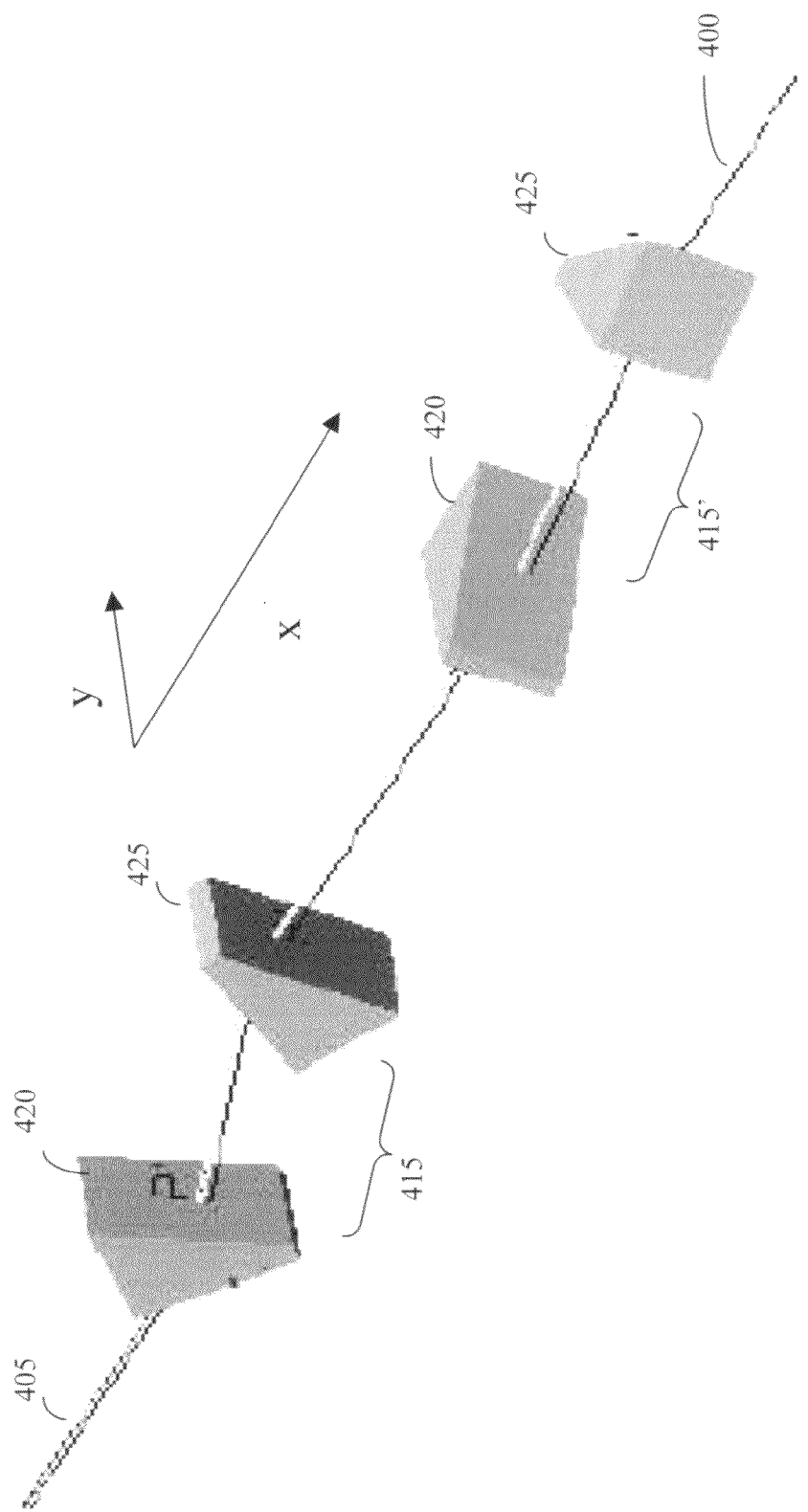
FIG. 4a illustrates an exemplary beam steering and shaping module according to the present invention, which enables adjustment of the position, angle, shape, and size of the upstream beam.

FIG. 4a illustrates an embodiment of a beam steering and shaping (BSS) module according to the present invention, which enables adjustment of the position, angle, shape, and size of the beam. Shaping is defined herein as spot size scaling (which can be performed in two orthogonal directions). The apparatus of the present invention provides for the combination of shaping and steering together. Prior methods and apparatus can provide shaping and steering independently but not together.

The beam shaping involves producing an outgoing elliptical beam 400 from an incoming circular beam 405, the elliptical beam having an exact aspect (max to min) ratio necessary to form a focused beam of an exact dimension in X and Y without adding any astigmatism, spherical or other monochromatic aberration during adjustment. The beam steering corrects the position of the outgoing beam due to drift of the incident beam off-axis, or angular deviations caused by adjustments to the beam ellipticity.

Figure 4B:
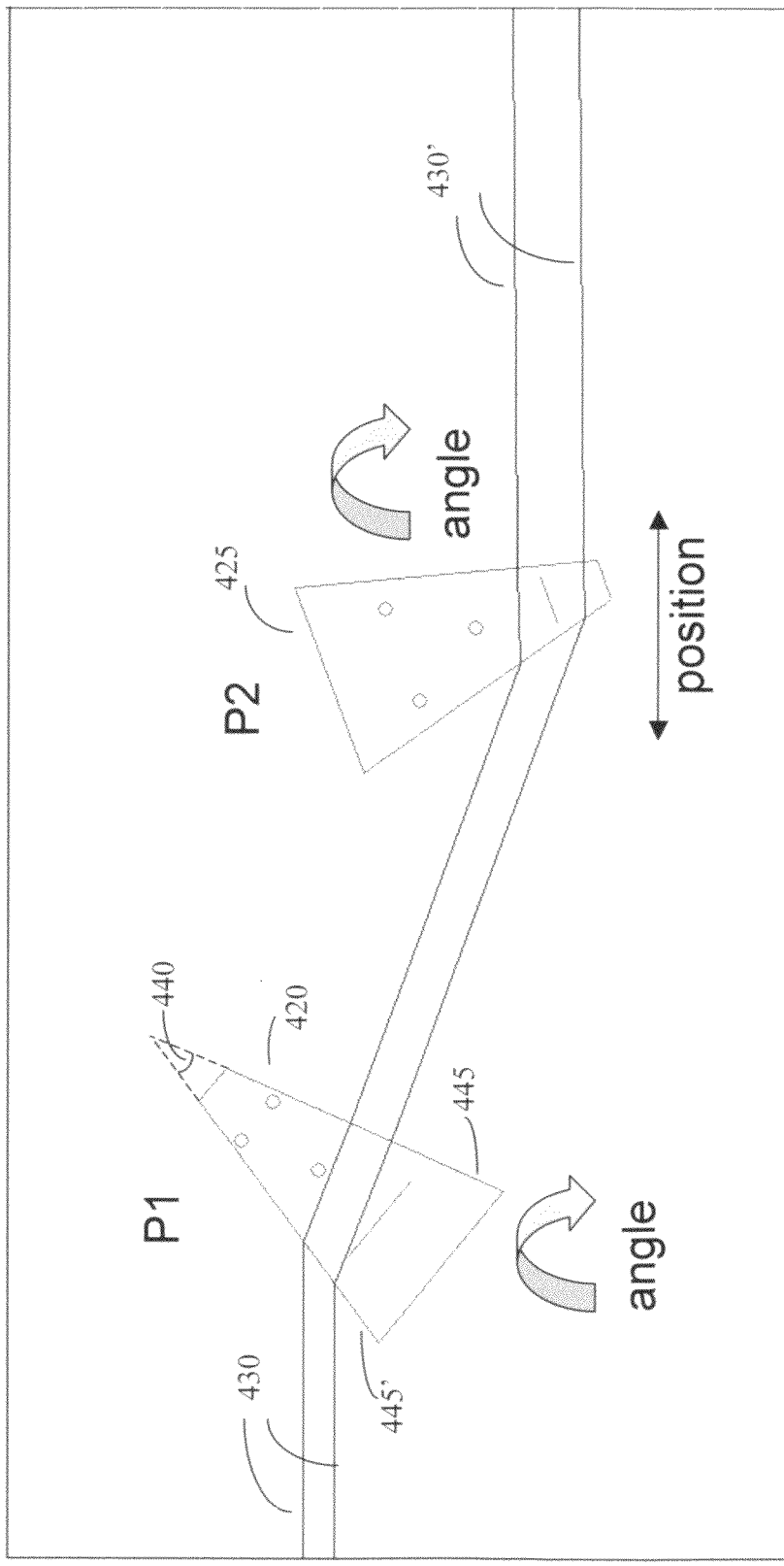

In an embodiment, the beam steering and shaping is performed using two orthogonally oriented pairs 415, 415' of prisms 420, 425 arranged in series. Depending on the source of the drift, a single prism pair may be sufficient. Also, to enhance the magnification range of the BSS, groups of three or more prisms could replace the prism pairs. A more detailed illustration of an exemplary prism pair is shown in FIG. 4b. The first element 420 of each pair 415 is rotating, the second element 425 of each pair is both rotating and translating, so as to affect both anamorphic magnification (beam ellipticity and spot size) and beam direction/shear (pointing angle and lateral offset). Note that the order of the rotating and rotating/translating prisms can be switched. Prism pair 415 performs the magnification (as illustrated by the expansion/contraction of light rays 430, 430') and deflection 435 in the x-direction (according to the axes shown in FIG. 5), whereas prism pair 415' performs the magnification and deflection in the y-direction. By being able to independently control both magnification and deflection in the x- and y-directions, beam position and ellipticity in the xy plane can be accurately controlled.

In this embodiment, the construction of the magnifier/demagnifier and beam steering mechanism is based on two pairs of thick prisms 415, 415' having wedge angles 440 of approximately 30 degrees with respect to surfaces 445, 445', such that the two surfaces 445, 445' of the prism elements, the surfaces which the light rays traverse, are optical quality polished, while the remaining four surfaces may be ground surfaces, similar to a lens.

An advantage of the inventive system over magnification systems that use lenses is that the afocal magnification of a simple lens pair (or two groups of elements) is a function of its lens groups' optical power or focal length (including group-to-group spacing), therefore only a single magnification can with no net focal power (i.e., afocal) be produced using a lens. In contrast, the same two prism elements can be adjusted to yield a range of magnifications by simply rotating the two elements in equal and opposite directions.

Figure 4C:
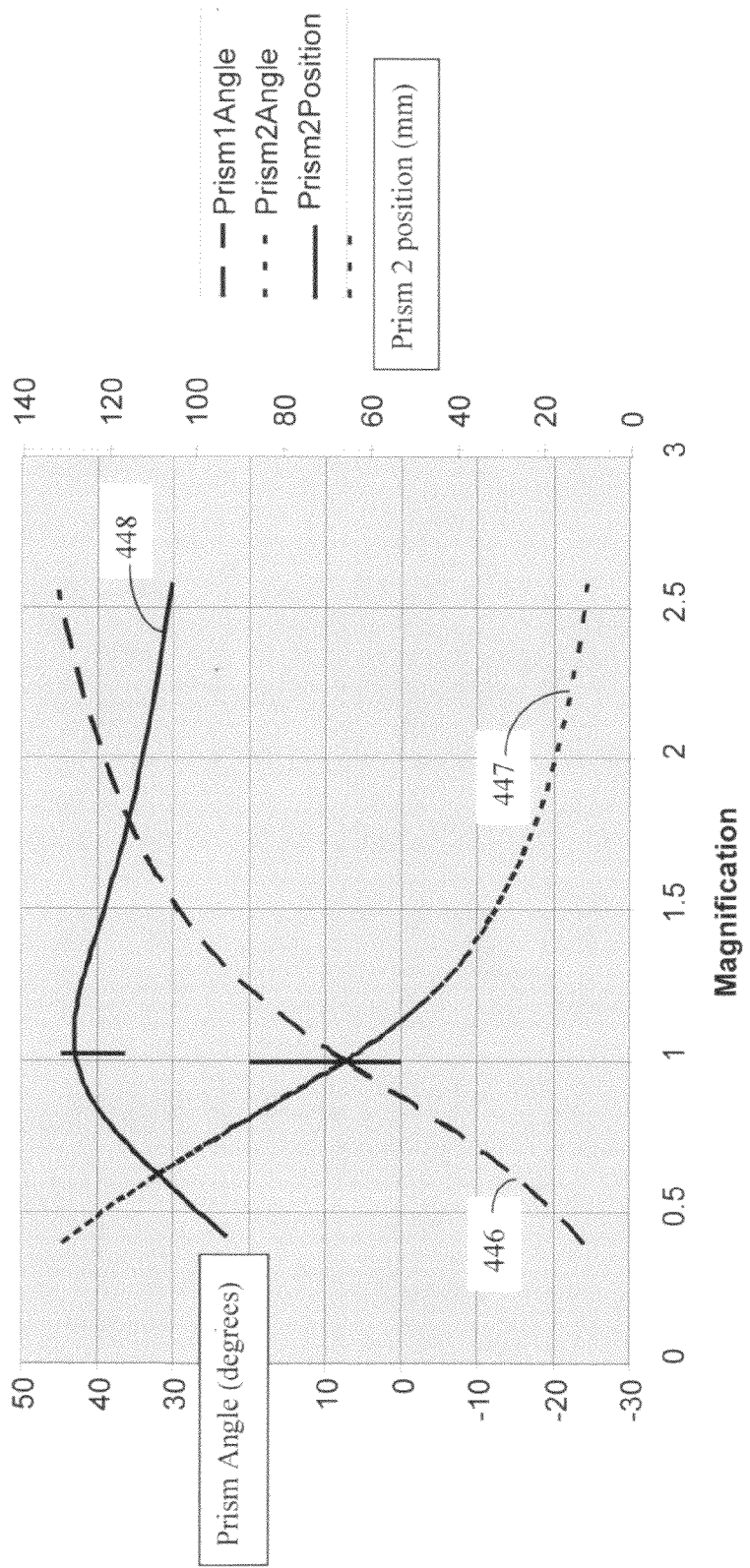
FIG. 4c is a graph of prism angle vs. magnification.

Each prism pair 415 acts as a telescope of a particular lateral magnification, depending on the angles of each prism (which is maintained perpendicular to the beam expansion/de-expansion axis), one prism following a clockwise rotation angle while the second prism follows a counter-clockwise rotation direction. FIG. 4c is a graph of prism angle and position vs. magnification, assuming a perfect incoming beam position and angle. Prism angle curves 446 and 447, and prism position curve 448, show the positions and angles required for a selected magnification, to eliminate shear and tilt for the outgoing beam. Note that there is a singularity at magnification 1, because magnification 1 can be achieved with an infinite number of prism positions, thus this magnification is avoided.

Figure 4D:
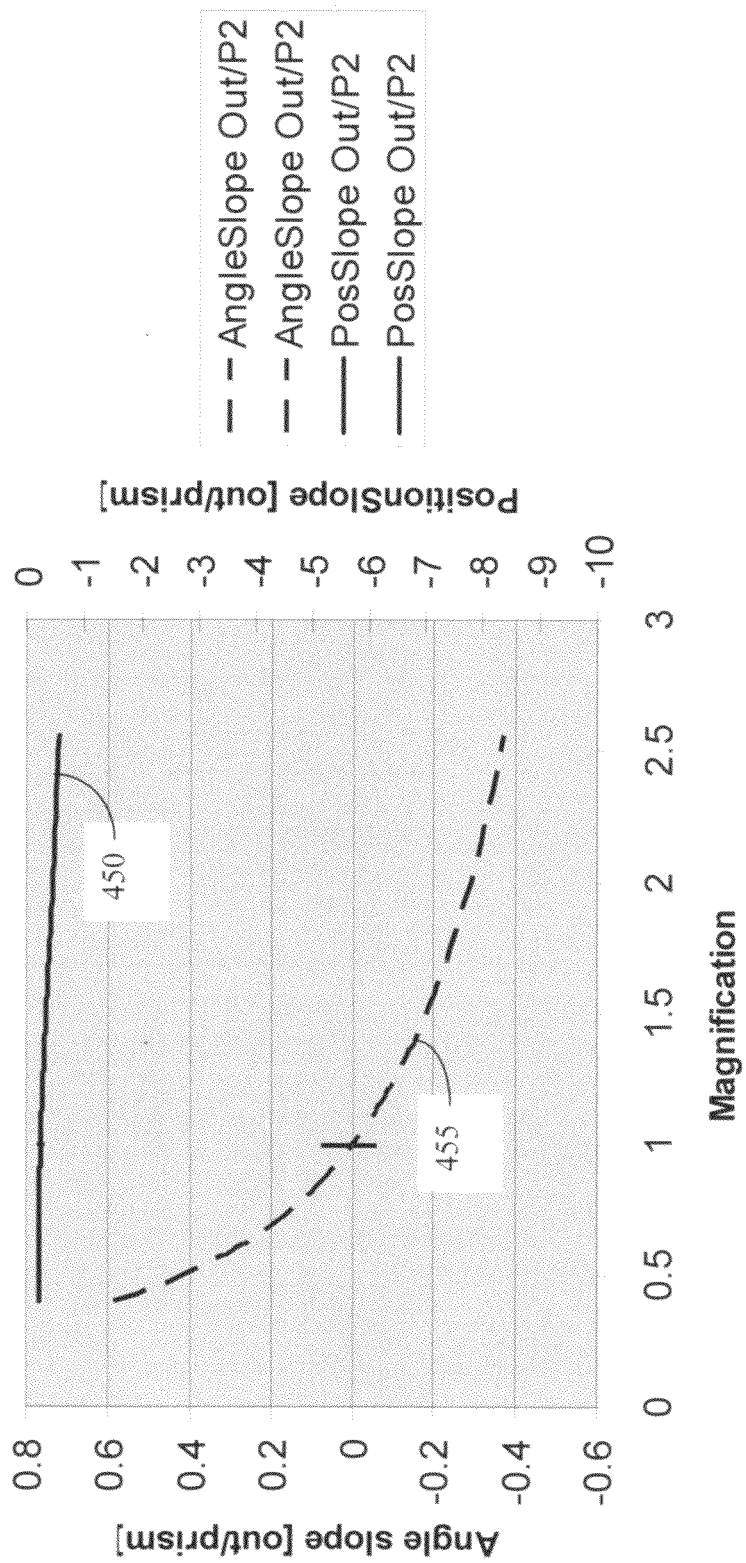
FIG. 4d shows the optical gain of the prism adjustment in terms of rotation and translation.

Errors or differences between the rotation angles of the two prisms produce a net beam angular deviation relative to the incident beam. This effect can be exploited to use the prism pair as a precise mechanism for correcting any errors in the incident beam angle. FIG. 4d shows how to compensate for tilt or position errors in the incoming beam. The figure graphs the optical gain of the prism adjustment in terms of rotation and translation. The Y axis is the ratio between the change in the output beam divided by the change in the prism (from the values shown in FIG. 4c for a "perfect" incoming beam). The translation curve 450 shows the ratio of beam output translation shift to prism translation shift. The curve is between 0 and −1, meaning the output shifts by less than the prism shift and in the opposite direction (for example 1 mm prism shift results in −0.5 mm beam output shift). The fact, that the output shifts by less than the prism adjustment, is a good thing, since it effectively gives better resolution. The angle adjustment curve 455 is similar: it shows how much the output pointing changes relative to the change in rotation of the prism. The values are also less than one and change sign with magnification. There is a singularity at magnification 1, because, as stated above, an infinite number of prism position combinations can achieve this magnification. That implies that at this position no angle adjustment is possible. Accordingly, magnification 1 is avoided.

Figure 5:
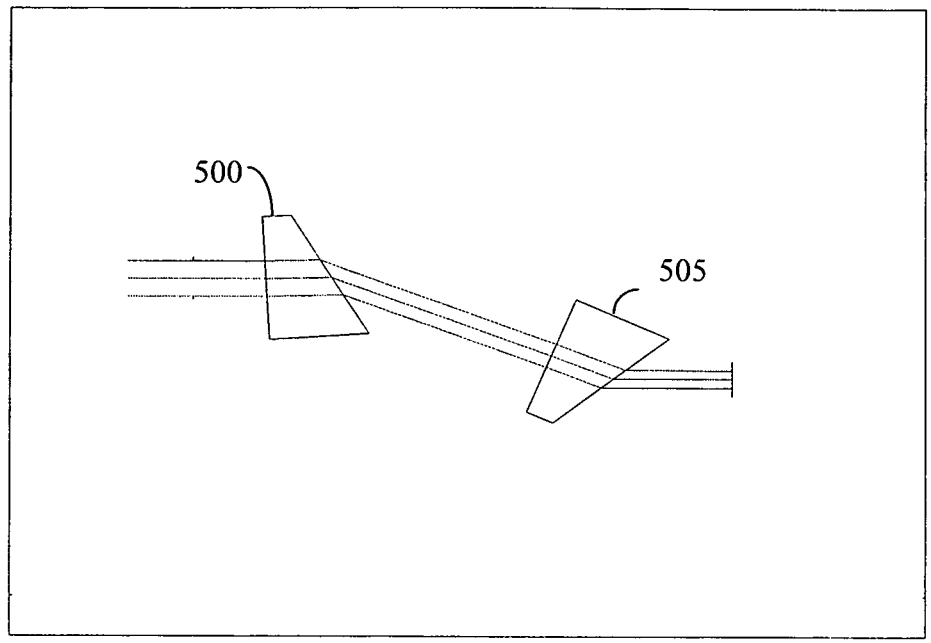
FIG. 5 illustrates prism rotations to produce magnification and angular deviation.
Figure 5:
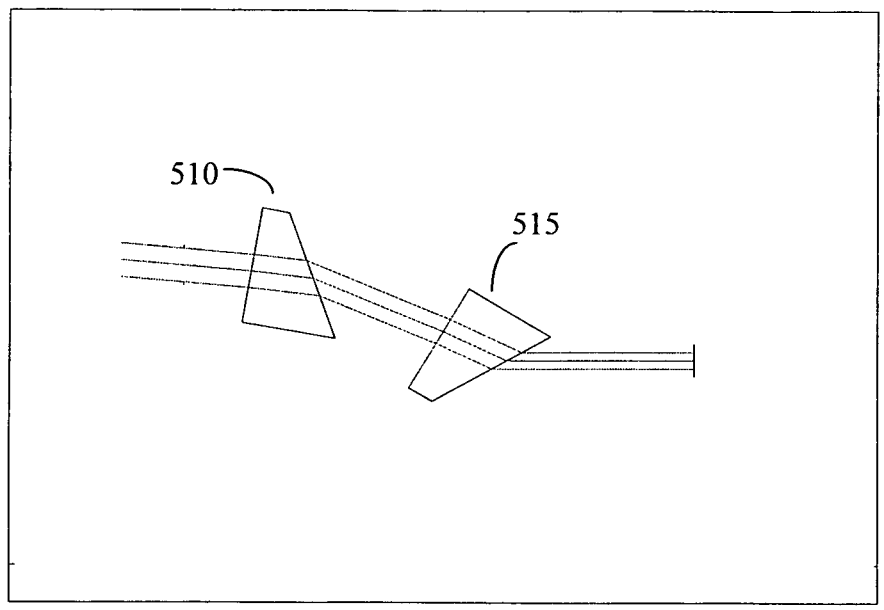

FIG. 5 illustrates prisms 500 and 505 rotated equally in opposite directions to produce a magnification effect only. In contrast, prisms 510 and 515 are rotated by unequal amounts, resulting in a combined magnification and angular deviation effect. Due to the complexity of the math, a look-up table is used to run the control loop, rather than using explicit formulas. The prism pair mechanism can also be used to correct errors if the incident beam points along the correct axis but the exiting beam is not parallel to the incident beam. Either of the above-mentioned errors can be corrected by having dual beam position sensors to measure the beam deviation angle and iteratively adjusting the beam size and steering mechanism to simultaneously minimize both magnification and pointing angle errors.

A second advantage of the inventive system is that beam magnification and steering are performed by the same set of elements. Prior systems performed beam shaping using two groups of cylindrical lenses, whereas beam steering was done with two separate motorized tip/tilt mechanisms using plano mirrors to produce the required beam angle and/or beam offset. In addition, the use of the wedge prisms of the present invention yields advantages over prior beam steering apparatus and methods as follows:

Traditional methods of beam steering require tilting a folding mirror about a transverse (X or Y) axis defined by each fold mirror mount's tip/tilt mechanism, which may not be orthogonal to each other. This can cause substantial errors in beam deflection. In contrast, the prism pairs of the present invention can only apply large beam deviations in a plane which contains the large wedge of the prism. (In the illustrative case, each prism has approximately 30 degrees of wedge). Therefore, even if there are errors associated with rotation of the prism about an axis not entirely in the plane of the wedge angle, the beam will only deflect, in terms of beam angle change, along the wedge angle. Since the wedge is precisely controlled and measured optically, out of plane wedge manufacturing error can be minimized quite easily. This means that cross-talk in tip/tilt mechanisms is greatly reduced, allowing centroid finding and alignment algorithms to have independent XY control. Although generally both prisms in each anamorphic prism pair assembly are rotated in opposite directions to maintain input to output beam parallelism, for small incident beam pointing errors, e.g., associated with thermally-induced laser drift, only one prism from each pair needs to be rotated to reestablish the correct optical beam axis: While there is a change in magnification with small rotation of the final prism in each prism pair, this error is small enough such that thermally induced changes in beam pointing only require steering adjustment using one prism and not magnification adjustment using both prisms.

Corrections to beam steering and shaping as described above can only be effectively implemented if accurate measurements of the beam position, size, and shape are available.

Previous measurement methods used PSD (Position Sensitive Detector) sensors at two distinct distances from the source to use for triangulation. This method can only measure the spot centroid, not the size or shape of the beam. CCD sensors can be used instead of the PSD's, however in magnifying the beam the fill the detector format, the sensitivity to angular deviation would be reduced. One disadvantage of the prior method is that, to measure very small angular deviations, the distance between the two sensors has to be quite large, and two sets of beam pickoffs are required to extract a fraction of the beam energy for centroid detection.

Figure 6:
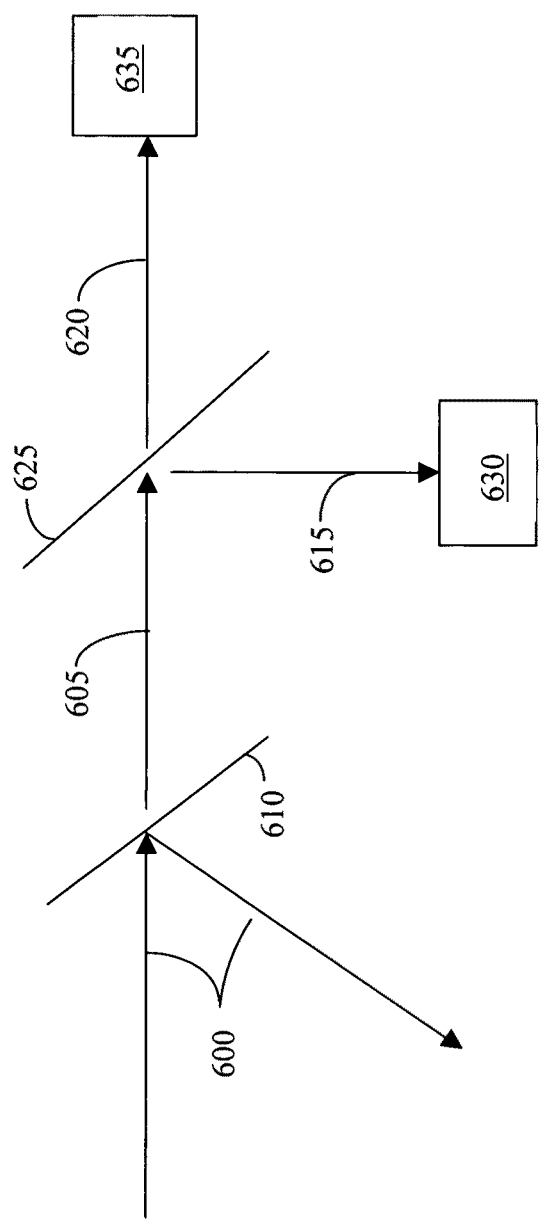
FIG. 6 illustrates an embodiment of the inventive beam monitoring and measurement system.

In an embodiment of the inventive beam monitoring and measurement system, illustrated in FIG. 6, a portion 605 of incoming laser beam 600 is leaked through partially reflecting fold mirror 610, then beam 605 is split into two channels 615 and 620 using non-polarizing beam splitter 625. Sensors such as cameras 630 and 635 are positioned on the two channels. The two channels 615 and 620 are optimized, one for measuring angle (tilt) and the other for measuring position (shear). This method provides simultaneous spot position and angle measurement, while eliminating one optical element, i.e., beam pickoff, from the illumination beam path. It also enables implementation of a control algorithm that provides feedback about the tilt and shear. The control algorithm is as follows: One camera measures tilt, i.e., the position of the beam on the camera (we measure the centroid of the beam) relative to a teach point (nominal position of the beam on the camera) tells us how much we have to adjust the output tilt.

This is done in a linear fashion: Output correction=AdjustmentGain*(actual position−nominal position). The adjustment gain is read from the calibration curves. This formula is applicable to both the tilt and the shear camera, the only difference is that they have to go to their respective table to find the proper adjustment. This process is done iteratively, meaning the system checks after the first adjustment and runs it again, if the output is not within the desired range (typically 1 uRad, generally somewhere between 0.1 uRad and 100 uRad).

Figure 7:
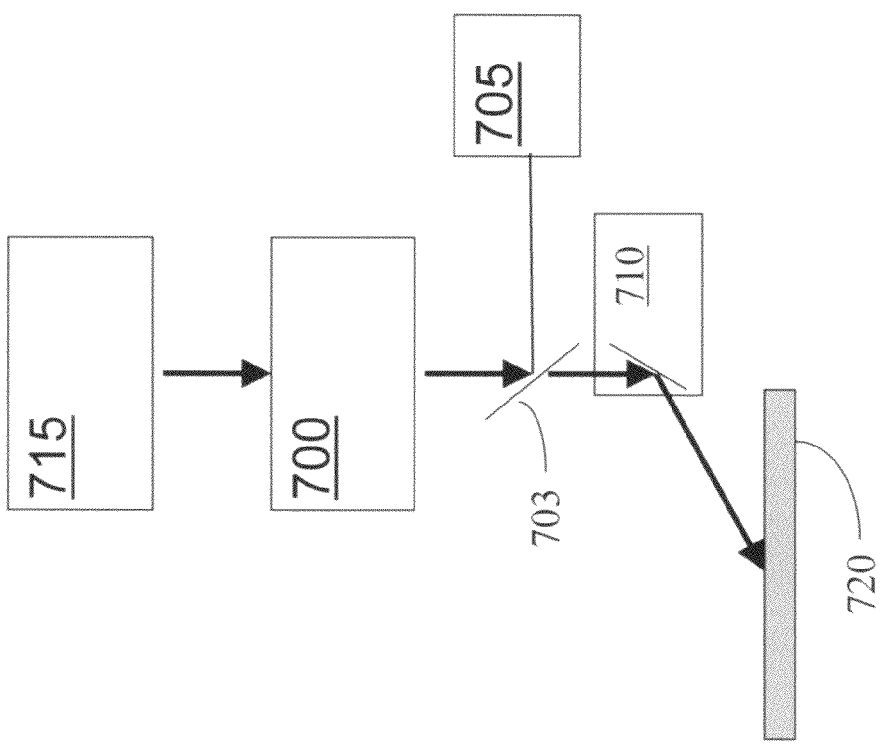
FIG. 7 is a block diagram showing an example of relative placement of the beam steering/shaping module, the measurement module, and the autofocus module, relative to the beam source and sample.

FIG. 7 is a block diagram showing an embodiment of the relative placement of the beam steering/shaping module 700, the measurement module 705 and beam splitter 703, and the autofocus module 710, relative to light beam source 715 and sample 720. In this embodiment the measurement module is at the output of the beam steering system and before the autofocus system. This particular relative placement of the modules is exemplary and not limiting.

The present invention provides substantial improvements to the oblique laser illumination for a spinning optical wafer inspection system. Front-end beam steering and shaping optimizes the position and spot size of the beam entering the system optics, which maximizes intensity and maintains resolution. An inventive measurement system provides feedback regarding both beam size, shape, and angle. Back-end beam steering is incorporated into a high-speed auto-focus mechanism.

It is not anticipated that the invention be limited to the exact embodiments described herein. Those skilled in the art will recognize that changes and modifications can be made without departing from the inventive concept. For example, other types of sensors than those mentioned can be used. The fast AF sensor could be quad cells, PSDs, various types of cameras, position sensitive PMTs. The BSS can use 2D cameras or sets of 1D cameras, or could use beam scanners of various incarnations. One could also imagine simpler implementations with no capability of shape measurement, where sensors as for the fast AF above are used. Alternatively, the first AF sensor and the BSS tilt sensor could be one and the same. Both measure the tilt angle. There are separate cameras in the embodiment described, because the AF has to be fast, so a fast 1D camera was used, while the BSS needs a 2D camera, which is typically slow. However, if an alternative detector was used that had 2 dimensions and was fast, or in an implementation of a simpler BSS system that corrects only 1 dimension, a common camera could be used.

The scope of the invention should be construed in view of the claims.

With this in mind, we claim:

1. A spinning wafer inspection system for inspecting a wafer surface including a high frequency fast auto focus mechanism, wherein;
   said high frequency fast auto focus mechanism dynamically adjusts tilt of a rotatable mirror to bring and maintain a laser beam focal spot onto said wafer surface; and;
   wherein there are no focusing optics in said laser beam's optical path between said rotatable mirror and said wafer surface;
   wherein said high frequency fast auto focus mechanism comprises a control system configured to utilize feedback from position-sensitive detectors to dynamically calculate actual beam position, actual position of said wafer surface, and intercept point between the beam and said wafer surface at any sampling time.

2. The inspection system of claim 1, wherein said mirror configured to be dynamically tilted to dynamically change an incidence angle of a laser beam incident on said wafer surface, said laser beam having a focal spot, so as to bring and maintain said focal spot onto said wafer surface, comprises a small off-optical axis AutoFocus (AF) mirror in the path of said incident laser beam.

3. The inspection system of claim 2, wherein said AF mirror is configured to be dynamically tilted by being mounted on a high stiffness piezo actuator with a high voltage amplifier.

4. The inspection system of claim 1, wherein said auto focus achieves response times less than 100 ms.

5. The inspection system of claim 1, further including a control system to control said auto focus mechanism.

6. The inspection system of claim 5, wherein said control system is configured to couple with said means for dynamically changing an incidence angle of a laser beam incident on said wafer surface and further configured to use feedback from an incident beam position-sensitive detector.

7. The inspection system of claim 1, wherein said high frequency fast auto focus mechanism is coupled to an actuator for causing low frequency z-motion of said wafer surface.

8. The inspection system of claim 4, wherein said auto focus achieves response times less than 10 ms.

9. A high frequency fast auto focus mechanism;
   said high frequency fast auto focus mechanism suitable for being used on a spinning wafer inspection system;
   wherein said wafer inspection system inspects a wafer having a wafer surface using a laser beam incident on said wafer surface at an intercept point;
   said high frequency fast auto focus mechanism dynamically adjusts tilt of a rotatable mirror to bring and maintain a laser beam focal spot onto said wafer surface;
   wherein there are no focusing optics in said laser beam's optical path between said rotatable mirror and said wafer surface; and;
   wherein said high frequency fast auto focus mechanism comprises a control system configured to utilize feedback from position-sensitive detectors to dynamically calculate actual beam position, actual position of said wafer surface, and intercept point between the beam and said wafer surface at any sampling time.

* * * * *